United States Patent [19]

Shepherd et al.

[11] Patent Number: 5,632,643
[45] Date of Patent: May 27, 1997

[54] ELECTRONIC CABLE YOKE SOCKET WITH LOCKING MECHANISM

[75] Inventors: David J. Shepherd, San Clemente; Harald O. Olms, Lake Forest; Henry G. Rossini, San Clemente, all of Calif.

[73] Assignee: Tronomed, Inc., San Juan Capistrano, Calif.

[21] Appl. No.: 596,647

[22] Filed: Feb. 5, 1996

[51] Int. Cl.$^6$ .................................................. H01R 13/62
[52] U.S. Cl. .......................................... 439/368; 439/346
[58] Field of Search .................................... 439/345, 346, 439/350, 351, 352, 355, 368

[56] References Cited

U.S. PATENT DOCUMENTS 4,227,762  10/1980  Scheiner .................................. 439/368

*Primary Examiner*—Neil Abrams
*Assistant Examiner*—Yong Ki Kim
*Attorney, Agent, or Firm*—Price, Gess & Ubell

[57] ABSTRACT

An improved yoke socket for use with separate leads and plugs such as those used with electrocardiogram devices provides detents to guard against accidental disconnection of plugs from the socket. A first surface of the yoke socket bears a row of apertures into which can be inserted connectors born by the individual lead plugs. A groove penetrates a second surface of the yoke socket to expose the inserted connectors. Each connector has a notch that acts in concert with a retaining rod placed within the groove to retain the plug against accidental detaching. The retaining rod comprises a series of expanded or bead-like portions connected by thinner rod portions. The expanded portion is sized to protrude into each aperture from the groove to serve as a detent by interacting with the notch of an inserted connector. The entire retaining rod is backed by a layer of compressed elastomer such as rubber which acts to bias the retaining rod into contact with the connector. A two piece plug combiner is also provided for temporarily aggregating a group of lead plugs into a single unit.

17 Claims, 6 Drawing Sheets

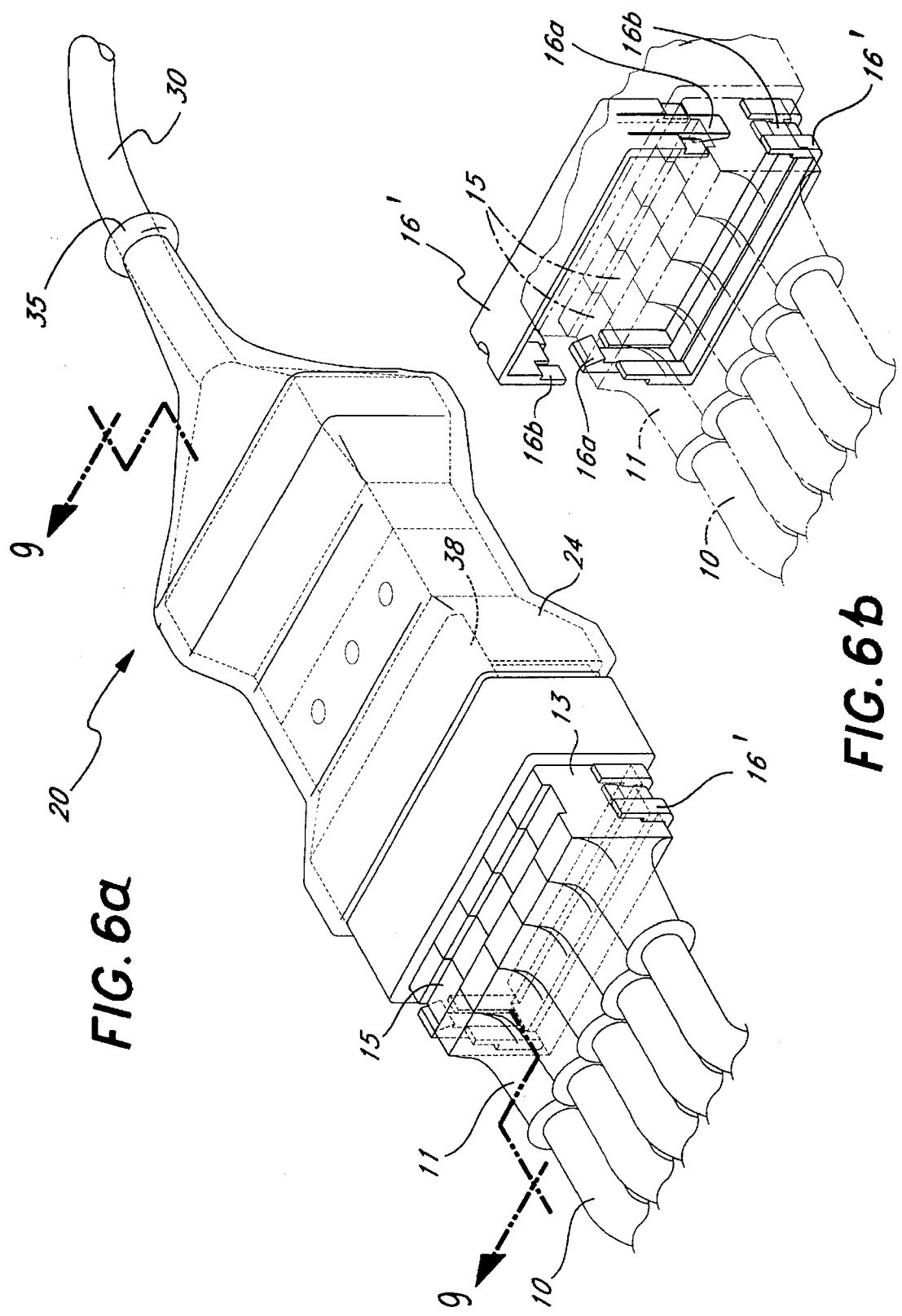

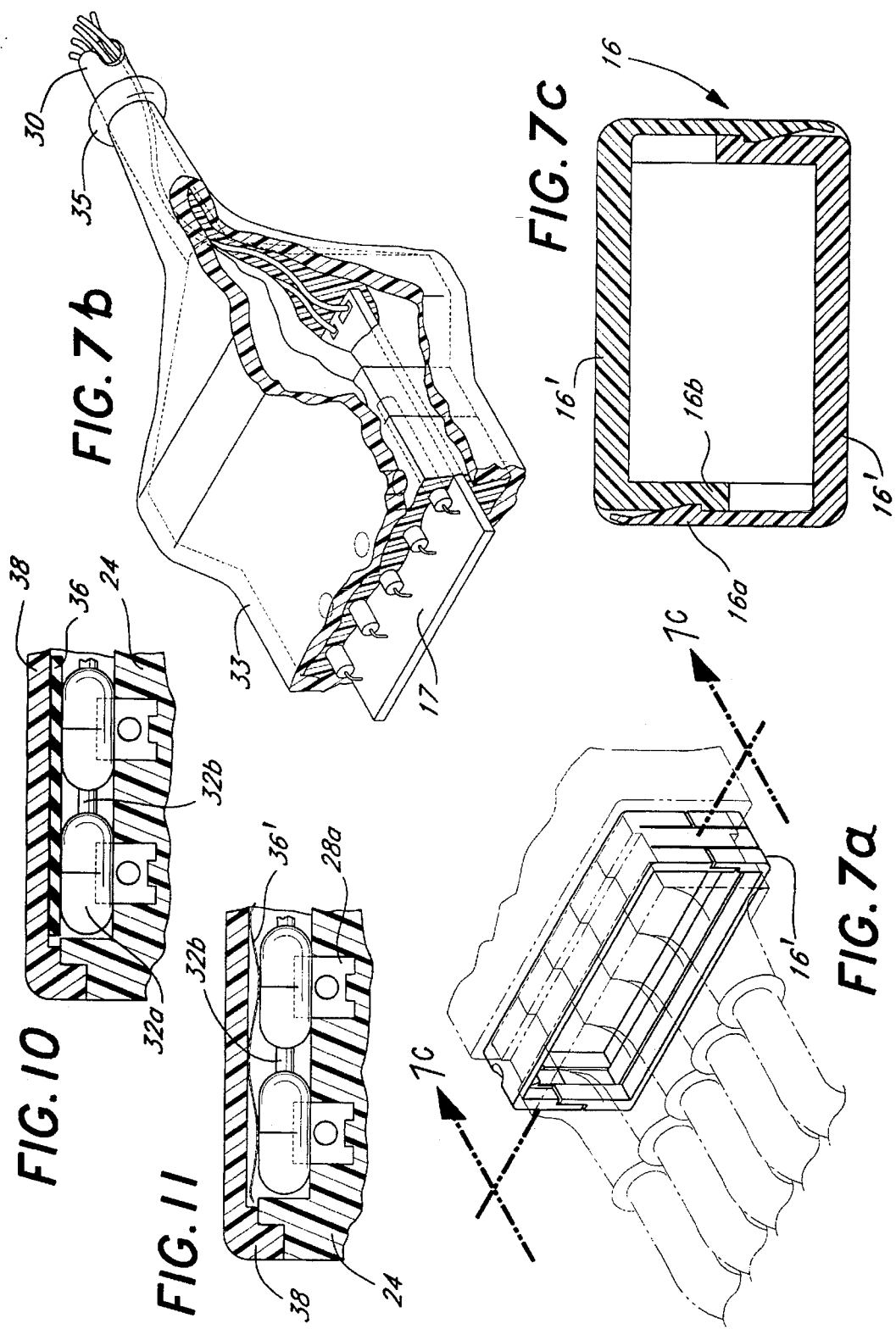

ELECTRONIC CABLE YOKE SOCKET WITH LOCKING MECHANISM

BACKGROUND OF THE INVENTION

1. Field of the Invention

The present invention concerns the field of electronic connectors and more specifically an improved cable yoke connector for retaining electrocardiogram or similar plugs against accidental disconnection.

2. Description of Related Art

There is a considerable need for reliable electrical plug connectors particularly in the field of medical testing equipment such as electrocardiogram (ECG) cables and leads. In such tests shielded leads are attached at one end to conductive pads attached at various points on the human body and at another end to lead connector plugs. The plurality of shielded lead connector plugs are then inserted into a common cable yoke socket on a common cable connected to a monitoring instrument. It is important that the various lead connector plugs be readily and securely attached to the yoke plug so that patient movement will not cause an inadvertent disconnection.

As might be imagined, there has been a considerable effort in the industry to produce standardized lead plug and yoke socket design, both to ensure adequate performance of various leads and cable yokes and to allow interchangeability between leads and yokes produced by different manufacturers. To this end an industry/clinician working group, the Association for the Advancement of Medical Instrumentation (AAMI), together with the American Nation Standards Institute (ANSI), has promulgated ANSI/AAMI EC53-1995, a standard for ECG leads, plugs, and yoke sockets. This standard defines the configurations of lead connector plugs and yoke sockets intended to accept those lead connector plugs. The standard allows the manufacturers a certain amount of design leeway as long as the leads and yokes otherwise meet the standard and remain interchangeable. Specifically, while the yoke/lead plug design specified in EC53 does not provide retention means to ensure against inadvertent removal of a lead connector plug from a yoke socket, the standard specifically encourages manufacturers to make modifications designed to provide retention forces to the cable yoke socket/lead plug combination.

The prior art has provided several different designs intended to ensure retention of lead plugs in yoke sockets similar to those used in ECG. For example, U.S. Pat. No. 4,913,667 to Muz describes a lead plug and yoke socket system including a casing intended to reversibly link together a group of lead plugs, as well as a yoke socket equipped with retention force enhancers intended to retain the lead plugs in the yoke socket against accidental disconnection.

In the Muz patent each lead plug is equipped with two separate connectors, one for a signal lead and one for a coaxial shield surrounding the signal lead. These separate connectors are shape-keyed (one round and one square) to ensure correct polarity and are joined by a single basal plug body. The square connector of each pair exhibits a recess or notch intended to interact with force retention enhancers when the connector is inserted into the cable yoke socket. These retention enhancers are provided by a blade stop spring having a free end segment received by the recess.

A potential problem with the blade stop spring is that should the spring become bent or fatigued, it will no longer provide adequate lead plug retention. Furthermore, a common free end segment is provided to interact with the several lead plugs that may be inserted into one cable yoke socket. This arrangement may provide an undesirable degree of mechanical interconnection between the individual lead plugs.

An additional feature in the above-cited Muz patent is a plug combinet which serves to aggregate a set of lead plugs into one convenient unit. Unfortunately, the plug combinet of this invention is a closed unit so that individual plugs are best slipped into the combinet prior to insertion in the yoke socket. However, this can be a clumsy operation since a plurality of plugs and leads must be held in the proper configuration until a lock strip on the combinet is closed.

OBJECTS AND SUMMARY OF THE INVENTION

It is an object of the present invention to produce a simple yoke socket design for use with ECG lead plugs and similar connectors;

It is an additional object of the present invention to provide an improved force retention locking mechanism for the yoke socket without requiring blade spring stops of the prior art; and It is a still further object of the present invention to provide the yoke socket locking mechanism that allows semi-mechanical isolation between the separate lead plugs which are inserted into the yoke socket.

It is an additional object of the present invention to provide a simple to use plug combiner that can be applied after the individual plugs are inserted into the yoke socket.

These and additional objects are met by an improved yoke socket for use with separate leads and plugs, such as those used with electrocardiogram devices, which provides detents to guard against accidental disconnection of plugs from the socket. The yoke socket bears a row of apertures into which can be inserted connectors born by the individual lead plugs. In addition, openings at approximately right angles to the apertures expose portions of connectors inserted into the socket. The exposed portion of each connector has a notch that acts in concert with a retaining rod within the yoke socket to retain the plug against accidental detaching. The retaining rod comprises a series of expanded or bead-like portions connected by thinner rod portions. The expanded portion is sized to protrude into an aperture through one of the openings interacting with the notch of an inserted connector and serving as a detent. The entire retaining rod is backed by a layer of compressed elastomer such as rubber which acts to bias the retaining rod into contact with the connector. Once the plugs are held by the yoke socket, a two piece plug combiner can be snapped in place onto the plugs to removably aggregate them into a single unit.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3 shows the yoke socket of the present invention with one of the lead plugs inserted therein;

FIG. 6a shows a finished socket and plugs of the present invention along with one half of a plug combiner;

FIG. 6b shows how the plug combiner is used to aggregate several lead plugs;

FIG. 7a shows a group of plugs aggregated by the plug combiner;

FIG. 7b shows a rear portion of a completed yoke socket;

FIG. 7c shows a cross-section of the plug combiner of FIG. 7a;

FIG. 10 shows a cross-section of the yoke socket illustrating a relationship between the beaded rod and the connectors of the lead plug; and FIG. 11 shows a cross-section of an alternative embodiment wherein a corrugated leaf spring serves as the resilient material.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a cable yoke socket which retains inserted lead plugs against inadvertent disconnection.

Figure 1:
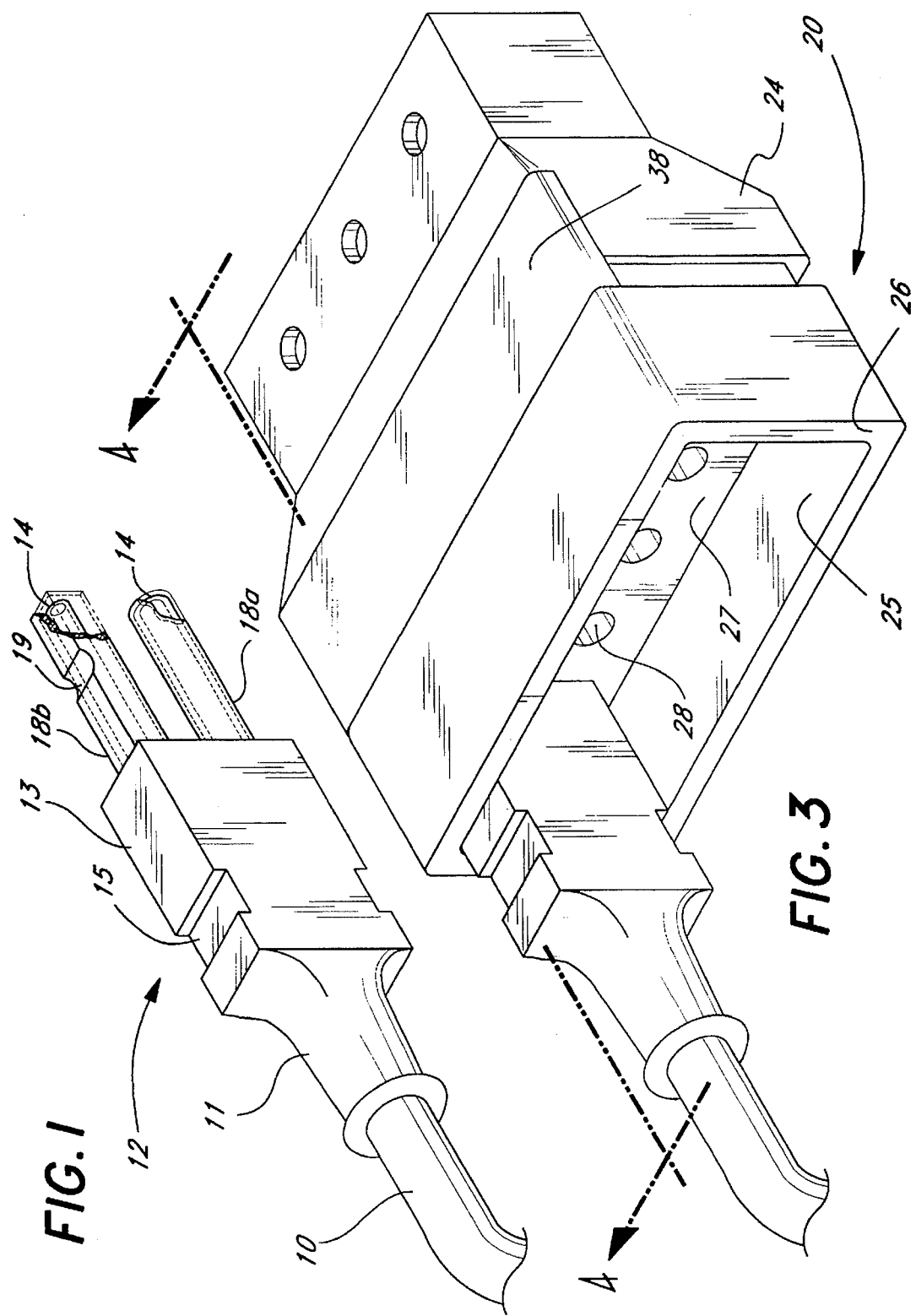
FIG. 1 shows a lead and a lead plug used in the present invention.
Figure 8A:
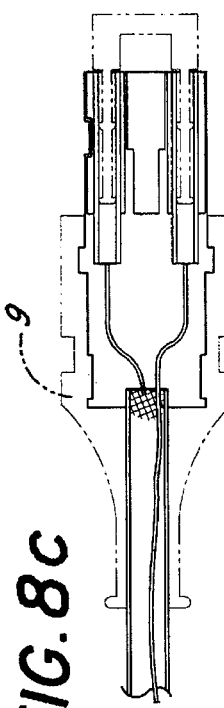
FIG. 8a show the first step in constructing the lead plug of the present invention.
Figure 8B:
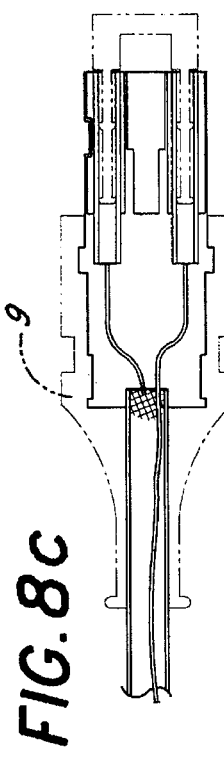
FIG. 8b shows the second step in constructing the lead plug.
Figure 8C:
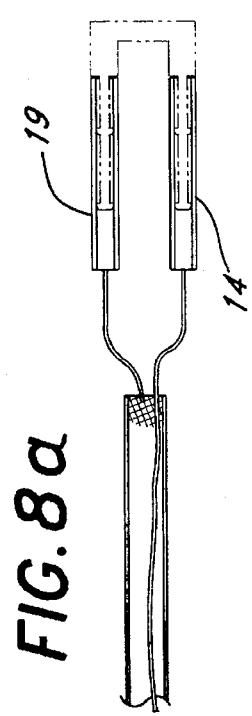
FIG. 8c shows the third step in constructing the lead plug.

FIG. 1 shows an ECG lead 10 and lead connector plug 12 which are compliant with Standard EC53 and can be used with a yoke socket 20 of the present invention. The lead 10 joins a lead plug base 13 surrounded a flexible rubber skin 9 that tapers into a strain relief 11. As shown in FIG. 8 this structure is preferably produced by attaching electrical conductors of the lead 10 to individual conductor sockets 14 (FIG. 8a) and then using an injection molding technique to form the lead plug base 13 and insulators 18 around the lead 10 and the individual conductor sockets 14 (FIG. 8b). Note that the insulators 14 are continuous with the lead plug base 13. This plug base-insulator assembly is then injection molded with a flexible rubber compound to form the rubber skin 9 and the strain relief 11 (FIG. 8c).

Each lead connector plug 12 comprises two conductive sockets 14 sized to accept conductive pins 22 and the associated insulators 18 which surrounds each socket 14 so that the sockets 14 cannot be accidentally shorted together. The insulators 18 of the two sockets 14 of each lead connector plug 12 are of different shapes so that signal polarity can be automatically maintained. The insulator 18a of the signal lead is round in cross-section, while the insulator 18b of the coaxial shield is square. A surface of the square insulator 18b opposite the round insulator 18a bears a rounded retention recess or notch 19 to help retain the connector plug 12 when it is inserted into the yoke socket 20.

Figure 2:
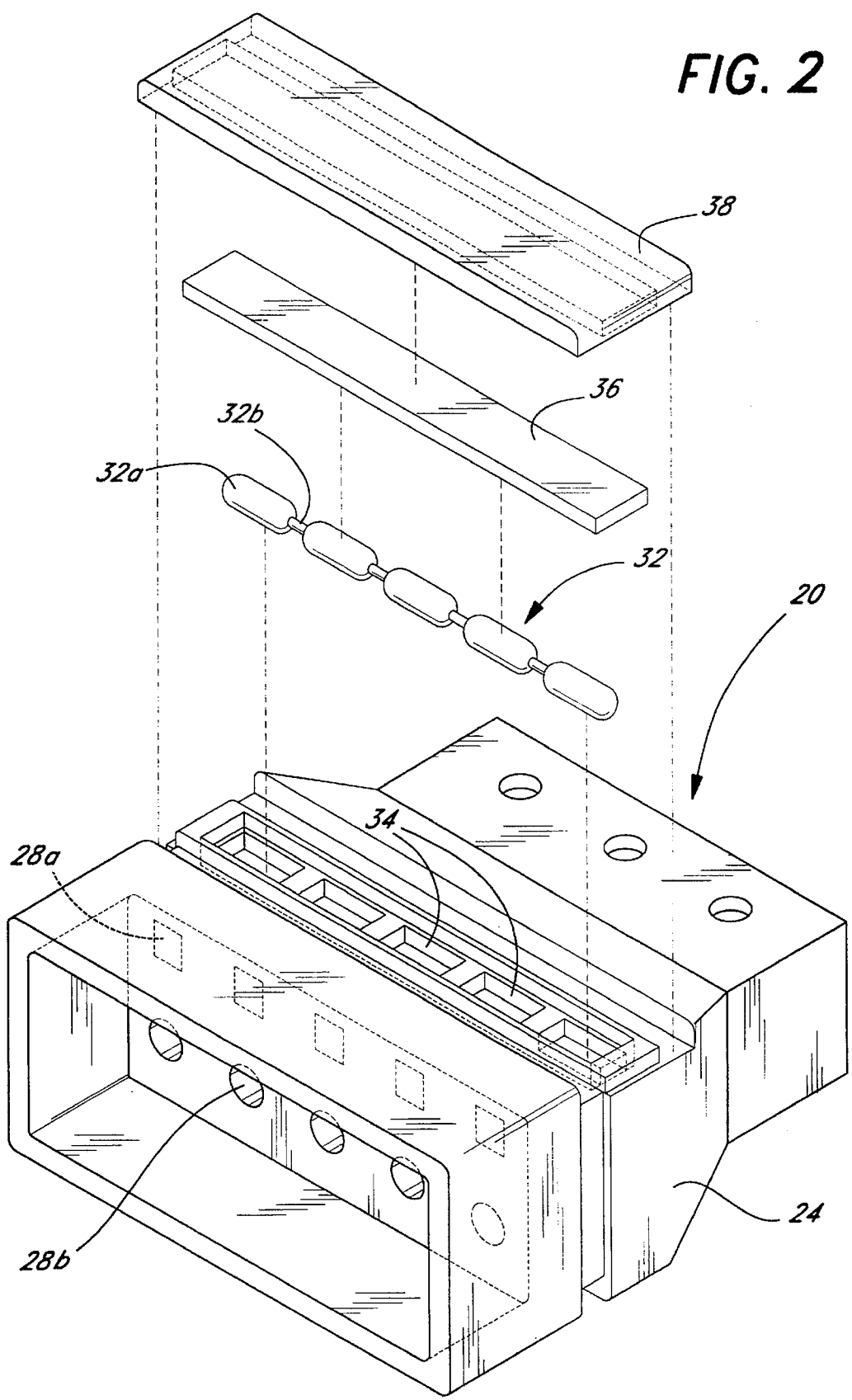
FIG. 2 illustrates an exploded view of a yoke socket of the present invention.

FIG. 2 shows an exploded view of the yoke socket 20. The yoke socket 20 can be produced as a two part "clam shell" configuration or, preferably, as a single injection molded part as illustrated. A yoke socket body 24 has a yoke socket 25 sized to accept a plurality of lead connector plugs 12. In this case the yoke socket 25 can accommodate five lead connector plugs 12, but the yoke sockets 20 can be readily manufactured to accommodate a larger or smaller number of lead connector plugs 12. The yoke socket 25 is defined by a collar 26 surrounding a front face 27 of the yoke socket body 24.

Figure 4:
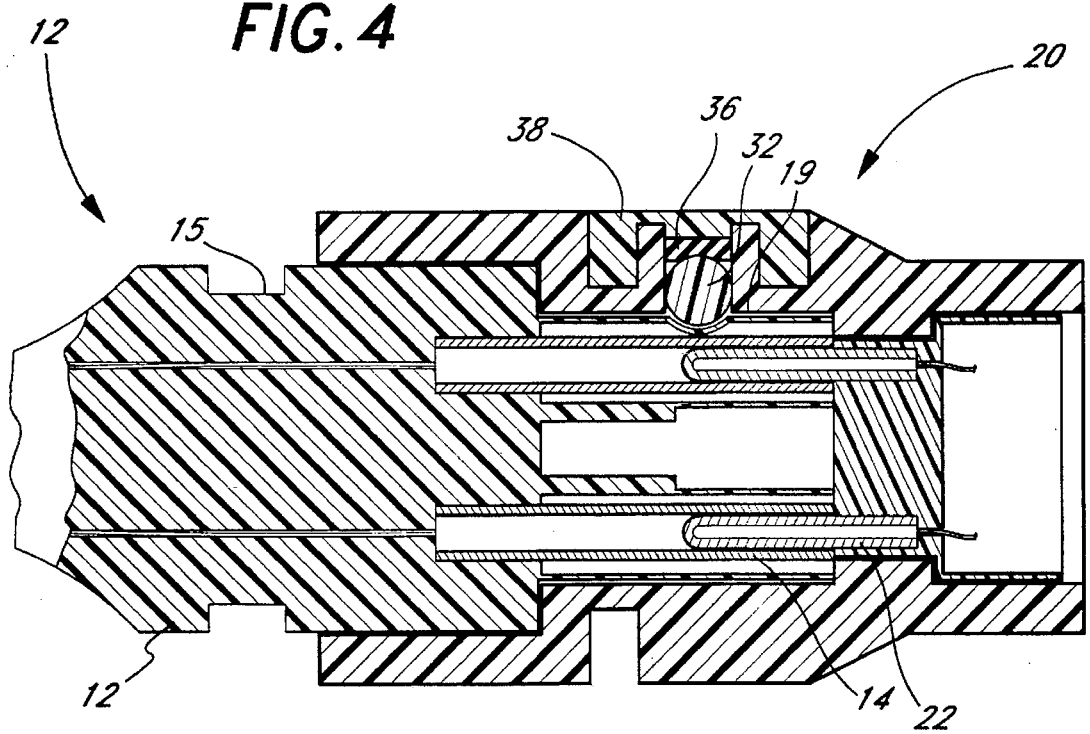
FIG. 4 shows a cross-sectional view of the lead plug inserted into the yoke socket.

As shown in FIG. 3, the collar 26 partially encloses the lead connector base 13 when the lead connector plug 12 is inserted into the yoke plug 20. The front face 27 bears pairs of apertures 28. The apertures 28 are the mouths of bores extending into the yoke socket body 24 and sized to fit the insulators 18 of the lead connector plugs 12. The round signal insulator 18a fits into a round aperture 28a while the square coaxial aperture 18b fits into a square coaxial aperture 28b. Conductive pins 22 are positioned centrally in each aperture 28 so that the pins 22 fit into the conductor sockets 14 when the lead connector plug 12 is inserted into the yoke socket 20 (see FIG. 4 for a cross-sectional view).

Figure 5:
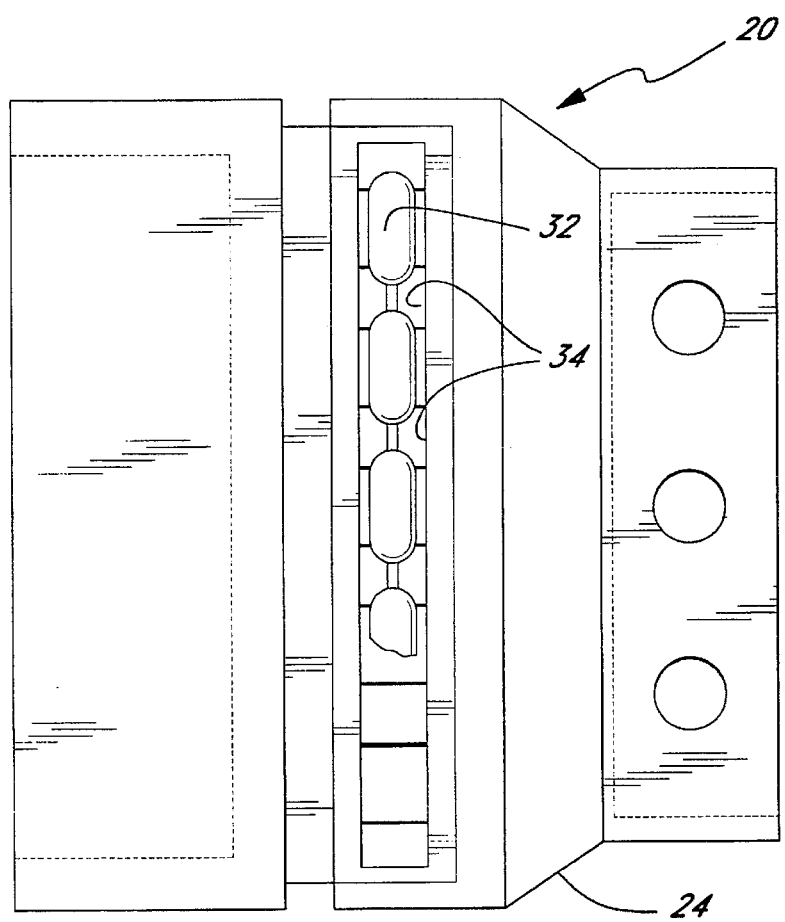
FIG. 5 shows a top view of the yoke socket of the present invention.

A beaded retaining rod 32 comprises a rod with a number of expanded "bead-like" sections 32a connected by straight sections 32b. The retaining rod 32 is inserted into the yoke socket body 24 so that the bead-like sections 32a are positioned to interact with the retention recesses 19 of inserted lead connector plugs 12. A top view, FIG. 5, of the yoke plug 20 shows that a series of openings 34 are provided, one for each square coaxial aperture 28b. When the retaining rod is inserted into the yoke socket body 24, the bead-like sections 32a extend into the openings 34 and lead connector plug 12 from the yoke socket 20. Although individual ball bearings backed by individual springs or by resilient material 36 would accomplish a similar function, individual ball bearings are much more difficult to contain than the retaining rod 32, especially during assembly. A uniform, rather than a beaded, rod may also be used; however, such a design does not afford mechanical isolation as does the preferred beaded rod 32.

After the locking mechanism which comprises the retaining rod 32, the resilient material 36 and the rod keeper 38 are assembled, a presently preferred way of utilizing the present invention is to attach the yoke socket body 24 to a small circuit board 17 to which a cable 30 is also attached. The circuit board 17 is sized to slide into slots (not shown) on an end of the yoke socket body 24 opposite the apertures 28. The circuit board 17 bears conducting pins 22 which are inserted into the yoke socket body 24 during the assembly procedure. The circuit board may also contain resistors and other electronic components that may be required for safety or noise suppression, etc.

Figure 9:
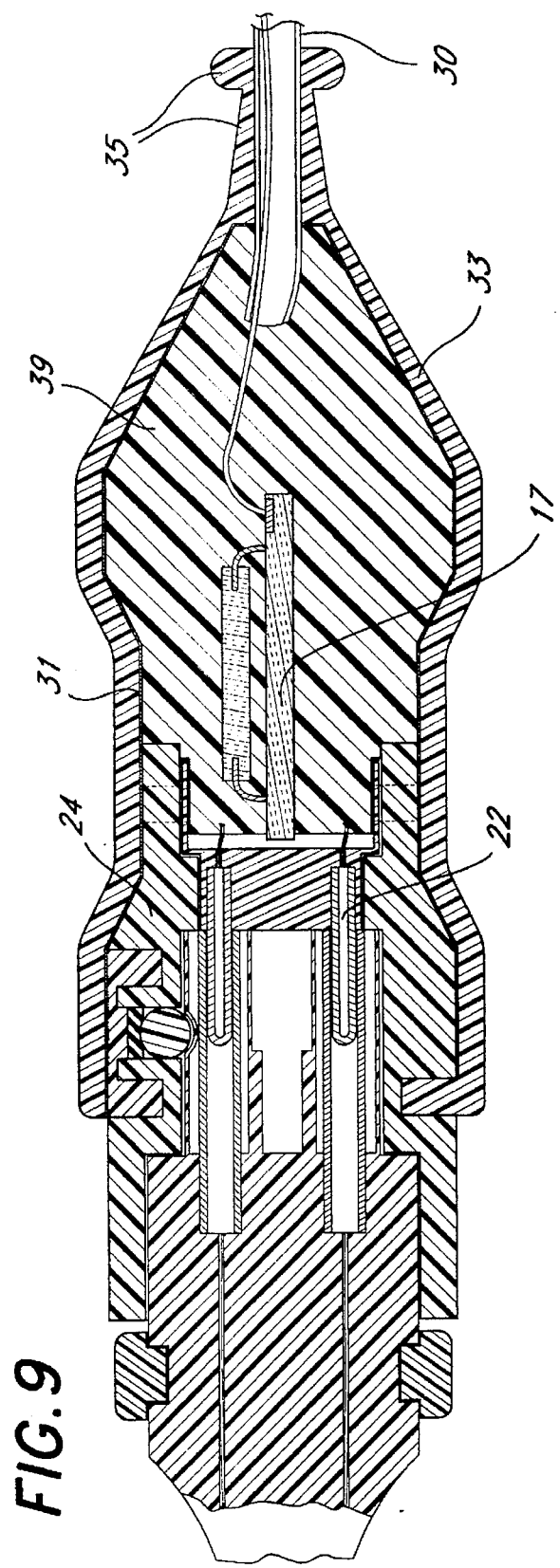
FIG. 9 shows a cross-section of part of the lead plug and the completed yoke socket of the present invention.

After the circuit board 17 is added, the yoke socket body 24 including circuit board 17 assembly is injection molded with polyethylene 39 to completely encase the circuit board 17 and seal it onto the yoke socket body 24 (see FIG. 9). This completed assembly is wrapped with metal foil 31 to provide electrical shielding. Finally the entire assembly is insert molded with a low durometer flexible rubber material 33 to provide an outer skin and strain relief 35 as shown in FIGS. 6a, 7b and 9. The final unit is totally sealed and protected by polyethylene 39 encasing the circuit board 17 and by the flexible rubber material 33 overcoating the polyethylene 39 and part of the cable 30.

The lead plug 12 bears recesses 15 that can be used with a lead wire combiner 16 to temporarily join a set of lead plugs 12 together. The lead combiner consists of two identical subunits 16' as shown in cross-section in FIG. 7c. Each subunit 16' has a barb 16a at one end and a catch 16b at a second end. The interconnection system is "hermaphroditic" in that the barb 16a of one subunit 16' mates with the catch 16b of another subunit 16.' Any two subunits 16' can latch together to for a complete combiner 16. The combiner 16 is most easily used after the lead plugs 12 are aligned by being inserted into the yoke socket 20 as in FIG. 6. The two pieces of the combiner 16 are then snapped together over the plugs 12. With the combiner 16 in place the aggregated plugs may be removed from and reinserted interact with the rounded retention recesses 19 of any inserted lead connector plug 12. The rod sections 32b are stopped by socket material between the openings 34 so that the retaining rod 32 does not protrude excessively into the square apertures 28b.

A layer of a resilient material 36 such as rubber is placed on top of the retaining rod 32 and a retaining rod keeper 38 is placed above and captures the resilient material 36. The keeper 38 is sized to compress the resilient material 36 which, in turn, presses on the retaining rod 32 biasing it into contact with any coaxial insulator 18b that is inserted into one of the coaxial apertures 28b. As the lead connector 12 is inserted into the yoke socket 20, a leading edge of the coaxial insulator 18b presses the bead-like section 32a of the retaining rod 32 up into the resilient material 36 until the retaining recess 19 aligns with the retaining rod 32. At that point the bead-like section 32a is forced into the retaining recess 19 where it acts as a detent to retain the lead plug 12 in the yoke socket 20 against accidental removal. FIG. 10 is a cross-sectional view illustrating the interaction between the resilient material 36, the keeper 38 and the beaded rod 32.

The rod sections 32b between the bead-like sections 32a are somewhat flexible, allowing individual bead-like section 32a a small amount of movement independent of the entire retaining rod 32. This affords some mechanical isolation between the detents of adjacent lead connector plugs 12 inserted into the same yoke socket 20. The degree of mechanical isolation of the individual plugs 12 depends on the resilient character of the material used to form the retaining rod 32. If the rod 32 is made from a more flexible, resilient plastic material, the degree of mechanical isolation is increased. It is also possible to mold or string the individual bead-like sections 32a onto a thin flexible fiber such as a nylon monofilament much like the construction of a strand of beaded curtain. In this case the bead-like sections 32a can be a very hard material with the flexible nylon interconnections allowing maximal mechanical isolation between the individual plugs 12.

The resilient material 36 can be natural rubber with a hardness of approximately 30 Shore A. Other elastomers of a similar springiness can be readily substituted for the rubber. Many suitable elastomers will occur to one of ordinary skill in the art such as urethane, neoprene, vinyl polymer, and silicone rubber. Alternatively, as shown in FIG. 11, the resilient material 36 can be a corrugated metal leaf spring 36', preferably with the corrugations spaced to optimally interact with the bead-like sections 32a. The interaction between the thickness of the resilient material 36, its hardness/elasticity characteristics, and the degree of compression caused by the keeper 38 all control the amount of force required to pull the retained into the yoke socket 20 as a combined unit. It is simple to bend one of the barbs 16a away from its mating catch 16b and separate the two subunits 16' to release the aggregated lead plugs 12.

Those of ordinary skill in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A yoke socket for removably retaining lead plugs when lead plugs are inserted into the yoke socket, the yoke socket comprising:

a yoke socket body having, on a first surface thereof, a row of apertures, each aperture sized to accept a connector of an individual lead plug, when a connector is inserted into one of the apertures and each aperture forming a mouth of a bore penetrating the socket body and sized to accept the connector;

a row of openings on a second surface of the yoke socket body, each opening penetrating the yoke socket body and intersecting one of the bores, each opening disposed to expose a connector surface when a connector is inserted into the bore which the opening intersects;

a beaded rod of alternating straight and bead-like regions, the bead-like regions spaced apart by the straight regions and sized so that the rod can be placed in contact with the yoke socket body with one of the bead-like regions intruding into each opening to lie within a retaining recess on a connector surface when a lead plug is inserted into one of the bores;

a piece of resilient material sized to cover the beaded rod; and a keeper sized to cover and compress the resilient material, biasing the bead-like sections to provide detents for retaining lead plugs when lead plugs are inserted into the yoke socket.

2. The socket of claim 1, wherein the resilient material is an elastomer selected from the group consisting of natural rubber, urethane, neoprene, vinyl polymer, and silicone rubber.

3. The socket of claim 1, wherein the resilient material is provided by a corrugated leaf spring.

4. A socket for removably retaining plugs, the socket comprising:

a socket body having, on a first surface, apertures forming mouths to bores sized to accept connectors born by the plugs;

a groove cut into a second surface of the socket body to expose a portion of a connector when one of the connectors is inserted into one of the bores;

a rod disposed within the groove and sized to interact with a retaining recess on an exposed portion of one of the connectors when one of the connectors is inserted into one of the bores;

a piece of resilient material sized to cover a portion of the rod; and means for compressing the resilient material, biasing the rod to provide a detent for retaining a plug in the socket when a plug is inserted therein.

5. The socket of claim 4, wherein the resilient material is provided by a corrugated leaf spring.

6. The socket of claim 4, wherein the resilient material is an elastomer selected from the group consisting of natural rubber, urethane, neoprene, vinyl polymer, and silicone rubber.

7. The socket of claim 4, wherein the rod comprises alternating sections, expanded bead-like sections interconnected by thinner sections and wherein the bead-like sections interact with retaining recesses.

8. The socket of claim 7, wherein the thinner rod sections comprise portions of a continuous flexible filament with the bead-like sections attached to the filament and spaced apart thereon.

9. A yoke socket system for removably retaining individual lead plugs, the yoke socket system comprising:
   a lead plug having at one end a connector with a retention recess on a lateral surface thereof; and
   a yoke socket comprising:
      a socket body having an aperture forming a mouth of a bore sized to accept the connector; and
      a locking mechanism comprising:
         a locking rod sized to fit the retention recess;
         a groove in the yoke socket, the groove penetrating into the bore and with the locking rod disposed in the groove to reach the retention recess;
         resilient material sized to cover the locking rod; and
         means for compressing the resilient material to bias the locking rod towards the retaining recesses providing a detent for stabilizing an interaction between the yoke socket and the lead plug when the plug is inserted into the yoke socket.

10. The socket system of claim 9, wherein the resilient material is an elastomer selected from the group consisting of natural rubber, urethane, neoprene, vinyl polymer, and silicone rubber.

11. The socket system of claim 9, wherein the resilient material is provided by a corrugated leaf spring.

12. The socket system of claim 9, wherein the rod comprises alternating sections, expanded bead-like sections interconnected by thinner more flexible sections and wherein the bead-like sections interact with the retaining recesses.

13. The socket system of claim 12, wherein the thinner rod sections comprise portions of a continuous flexible filament with the bead-like sections spaced apart thereon.

14. The socket system of claim 9 further comprising connection recesses on the lead plugs and a plug combiner including two interconnectable combiner sections for connecting together around the lead plugs and temporarily aggregating the lead plugs into an assembly by interacting with lead plug connection recesses.

15. The yoke socket system of claim 14, wherein the two combiner sections are identical.

16. A yoke socket system for removably retaining lead plugs, the yoke socket system comprising:
   lead plugs comprising:
      leads;
      lead plug bodies with connection recesses, one of the leads attached to a first end of each of the lead plug bodies; and
      connectors with retention recesses on a lateral surface thereof, one of the connectors attached to a second end of each of the lead plug bodies;
   a yoke socket comprising:
      a socket body having an aperture forming a mouth to a bore sized to accept one of the connectors; and
      a locking mechanism comprising:
         a locking rod sized to fit the retention recess;
         a groove in the yoke socket penetrating into the bore with the locking rod disposed in the groove to reach the retention recess;
         resilient material sized to cover the locking rod; and
         means for compressing the resilient material to bias the locking rod towards the retaining recesses providing a detent for stabilizing an interaction between the yoke socket and the lead plug when the plug is inserted into the yoke socket; and
   a plug combiner comprising two interconnectable combiner sections for connecting together around the lead plugs and temporarily aggregating them into an assembly by interacting with the connection recesses.

17. The yoke socket system of claim 16, wherein the two combiner sections are identical.

* * * * *